US005086629A

United States Patent [19]

Dibrell

[11] Patent Number: 5,086,629

[45] Date of Patent: Feb. 11, 1992

[54] SCARF FOR TRANSFERRING HEAT FROM OR TO BODY AREAS OF THE WEARER

[75] Inventor: Carroll M. Dibrell, San Antonio, Tex.

[73] Assignee: Exer Icer Towels, Inc., San Antonio, Tex.

[21] Appl. No.: 723,119

[22] Filed: Jun. 28, 1991

Related U.S. Application Data

[63] Continuation-in-part of Ser. No. 565,786, Aug. 13, 1990.

[51] Int. Cl.$^5$ ............................................. F25D 23/12
[52] U.S. Cl. ...................................... 62/259.3; 62/530; 128/403; 128/399
[58] Field of Search ...................... 62/259.3, 529, 530; 2/91; 128/399, 402, 403; 604/113; 126/204

[56] References Cited

U.S. PATENT DOCUMENTS 3,802,215  4/1974  Rowe .................................. 62/259.3
5,005,374  4/1991  Spitler ................................ 62/259.3

Primary Examiner—Albert J. Makay
Assistant Examiner—John Sollecito
Attorney, Agent, or Firm—Hubbard, Thurman, Tucker & Harris

[57] ABSTRACT

A scarf for wrapping around the neck or any other body portion comprises a longitudinally folded band of material which is transversely sewed to provide a plurality of pockets in the medial portion. The inner wall of each of the pockets is cut away and replaced by a thin sheet of material having greatly improved heat transmission properties. In a preferred embodiment, the sheet material is permeable to water vapor, but not to water. In another preferred embodiment, a pocket for ice particles is formed from the aforementioned vapor permeable, water impermeable, plastic sheet material and secured to the medial portion of the scarf.

11 Claims, 6 Drawing Sheets

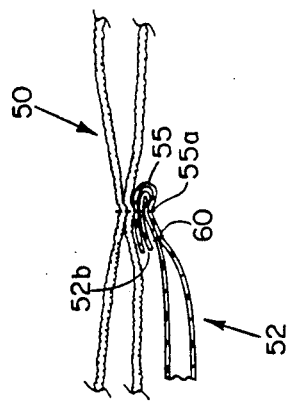
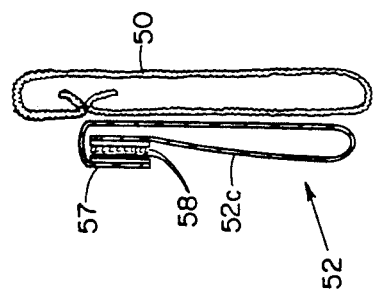
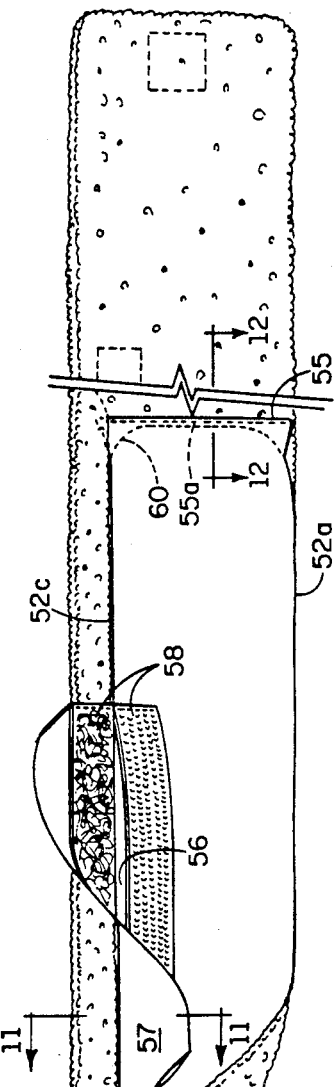
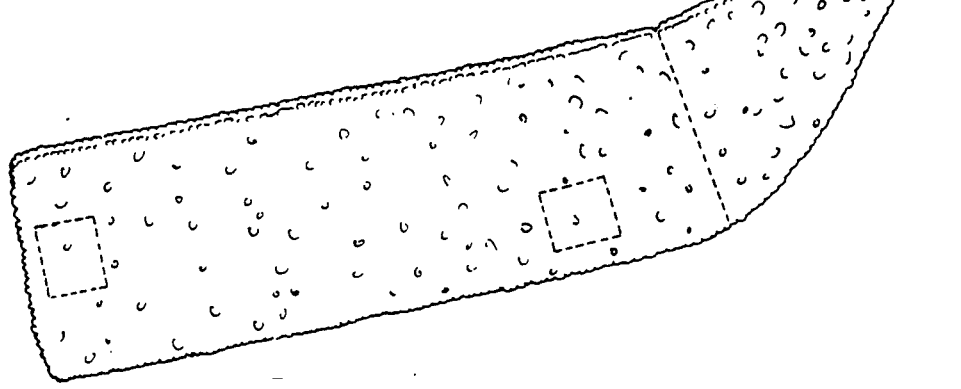
FIG. 12
FIG. 11
FIG. 10

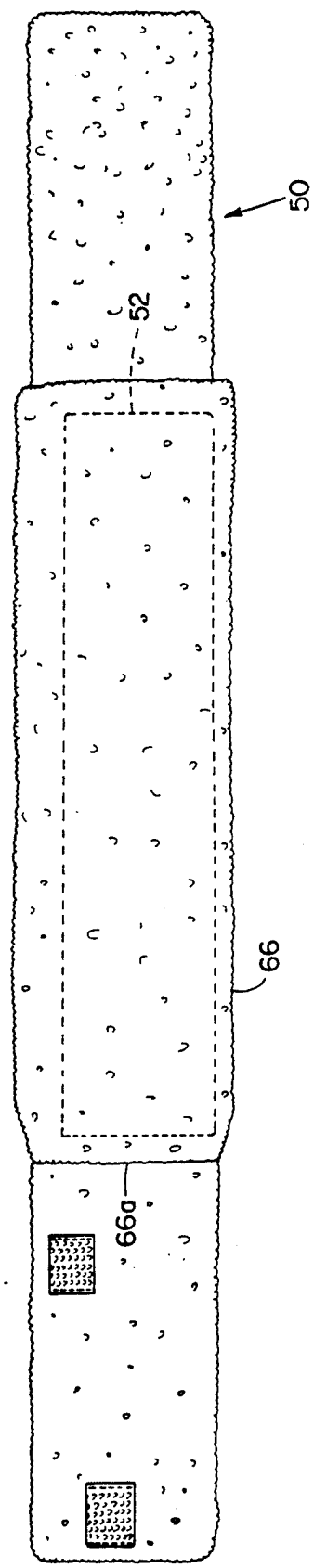
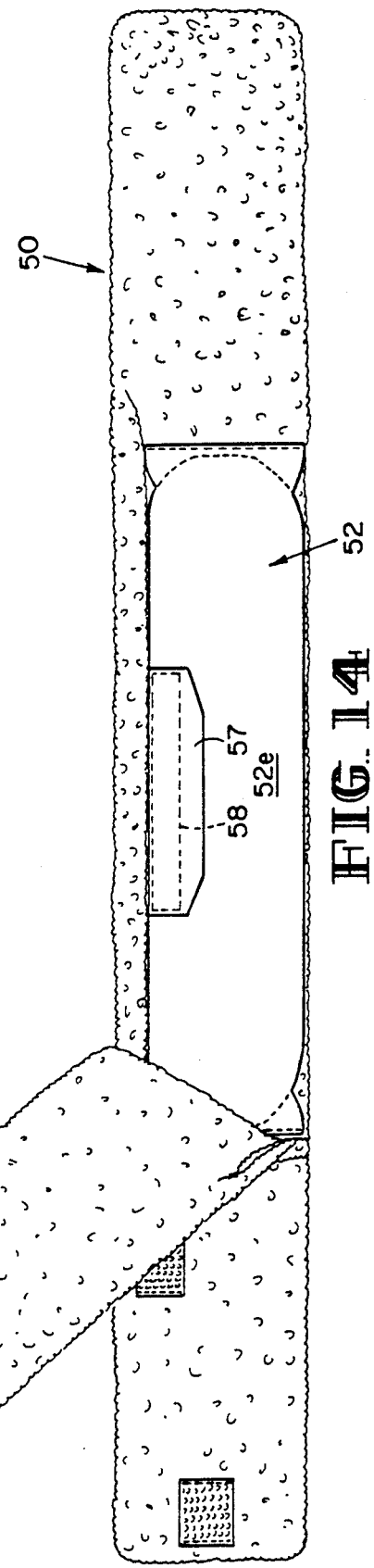
FIG. 13
FIG. 14

SCARF FOR TRANSFERRING HEAT FROM OR TO BODY AREAS OF THE WEARER

RELATIONSHIP TO COPENDING APPLICATION

This application constitutes a continuation in part of pending application Ser. No. 565,786, filed Aug. 13, 1990.

BACKGROUND OF THE INVENTION

1. Field of the Invention

The invention relates to a scarf which may be wrapped around the neck or other body areas of the user to perform a heat transferring operation on the body areas that the scarf contacts.

2. Summary of the Prior Art

A very familiar sight is an athlete coming off the field or court literally soaked in perspiration and needing a rapid cooling of his obviously elevated body temperature produced by the exercise. Generally the first thing that the athlete avails himself of is a towel which he wraps around his neck to remove the excess moisture and to concurrently exert a cooling effect on his neck. Towels have heretofore been provided with pockets for reception of crushed ice which improves the cooling action of the towel; however, the toweling material is an effective insulator and prevents any rapid absorption of heat from the wearer's neck into the mass of ice contained within the toweling material.

There is, therefore, a definite need for a scarf-like wrapping which can contain a heat absorbing material and efficiently absorb heat from a body area to which it is applied.

A similar problem arises for people who exercise during the winter and need protection against the cold, particularly when starting their exercise period. Pads of chemically activated materials have been heretofore available which can be placed in the pocket of a hunting jacket and which generate heat to keep the hands of the user warm. Such heat emitting pads have not, to Applicant's knowledge, been incorporated in scarfs for transmitting heat directly to the neck of the user where it more efficiently assists in maintaining the body temperature. Here again, there is a definitive need for an efficient transmission of heat from the heat emitting mass to the neck of the user, while at the same time providing insulation that reduces the outflow of heat into the atmosphere.

Thus the problem of efficiently removing heat from, or applying heat to a particular body area has not been effectively resolved.

SUMMARY OF THE INVENTION

This invention provides a scarf for efficiently transferring heat from or to any body area of the wearer to which the scarf can be applied, but particularly to the neck areas of the wearer. The scarf comprises an elongated band of a flexible fabric material which is wrappable around a body area of the wearer, such as the neck, and has reasonable heat insulating and water absorption properties, such as towelling. One or more pockets are formed on the medial portions of the fabric band and each pocket is provided with a selectively openable and closable opening by which a mass of heat absorbing material or heat transmitting material may be inserted. For heat absorption, ice cubes, crushed ice or a plastic encapsulated frozen gel may be used. For heat transmitting, a heated block of stone or metal, or a heated gel pack may be employed.

The inner wall of each pocket also has an elongated opening of substantial area formed therein and a sheet of thin gauge, heat transmitting material is secured across such pocket opening. Thus, the heat transmitting material is always placed in direct contact with the body area from or to which heat transfer is desired. The thin gauge, heat transmitting material permits the ready flow of heat from the adjacent body area to the heat absorbing mass contained within the pocket, or conversely, from a heat emitting mass in the pocket to the adjacent body part.

In one embodiment of the invention, the scarf is formed of a elongated piece of towelling which is longitudinally folded to provide an inner wall and an outer wall. Transverse seams are formed at longitudinally spaced intervals in the medial portions of the folded towel to define pockets for reception of a heat absorbing material, such as ice cubes, crushed ice or the frozen gel pack previously mentioned. The inner wall of such pocket is, however, cut away to provide an opening of substantial area and this opening is then closed by a thin sheet of flexible heat transmitting material. Such heat transmitting material may be a plastic or metallic foil, a thin gauge cloth, but is preferably a moisture or vapor permeable, thin gauge, flexible plastic material.

In another modification of the invention, a pocket of a moisture barrier, breathable, flexible plastic material is secured to the towelling.

The free ends of the towelling material defining or mounting the aforementioned pockets are provided with reclosable fasteners, such as opposed strips sold under the trademark "VELCRO" thus providing assurance that the mass of heat absorbing or transmitting material will not drop out of the pocket during use.

In one preferred form of the invention, ice cubes or crushed ice is employed as the heat absorbing material and a thin gauge, water permeable sheet of plastic material forms the inner wall of the pocket. This permits the cold water produced by the melting of the crushed ice to traverse the permeable wall and directly contact the body area to which the scarf is applied. You thus have a substantially greater removal of heat from the contacted body area. The fact that water may drip from such body area is generally of no consequence since vigorous exercise results in the athlete's body being literally covered with perspiration. In any event, the towelling material forming the major portion of the band can be employed to mop up any water drippings.

For people who do not greatly perspire, or who do not wish to have the water from the crushed ice flowing onto the body area, the use of the frozen gel packs or a non-permeable sheet will provide a substantial heat transfer without producing additional liquid. Such gel packs are well known in the market and may, for example, comprise the pack sold under the trademark "BLUE ICE" by Pelton Shepherd Industry of Stockton, California, or the "MICRO-FREZ" pack sold by Aerobe Automation Technology, Inc. of El Cajon, Calif. As is well known, these gel packs may be repeatedly used merely by inserting the pack in a domestic freezer or the ice making compartment of a refrigerator.

In another embodiment of the invention, the heat transmitting sheet or window is fabricated from a breathable, water impermeable, flexible plastic material, sold under the trademark "GORETEX" by W. L. Gore and Associates of Elkton, Md.. Such material may be aligned in the scarf to permit perspiration vapor to pass into the pocket containing ice particles and ice water, but will prevent reverse flow of ice water onto the body part through the plastic Alternatively, the ice containing pockets may be lined with the aforesaid "GORE-TEX" material, or the entire pocket may be fabricated of "GORETEX" material.

In a further embodiment of the invention, the aforedescribed scarf with the pockets having body contacting walls of thin gauge, heat transmitting flexible material, may be employed to effect the warming of the body area for use during cold weather. Obviously, the mass inserted into the pockets will be a heated mass which can comprise a heated gel pack, heated stones, a heated piece of metal, or a plastic bag of heated metal shot. Alternatively, chemical packs are known in the market which, when preliminarily heated or moistened with water, will emit heat for a substantial period of time and these packs may be inserted in the aforedescribed pockets. In any case, the body area around which the scarf is wrapped will be subjected to heat flow into such area produced by the heat emitting masses contained within the pockets.

Further embodiments of this invention are particularly useful to joggers or walkers who would customarily wear a heat transfer scarf around their neck for the purpose of cooling their body during their exercise Since many persons do their walks or runs at night, the external portions of the scarf which are exposed to the atmosphere when the scarf is wrapped around the neck of the person may have a plurality of patches or strips of highly colored light reflecting materials adhered thereto to provide increased visibility of the jogger or walker to the drivers of approaching vehicles.

In still another embodiment of the invention, the end portions of the scarf are formed with closable pockets for the carrying of certain accessories which some joggers deem to be very vital to their health and safety. For example, a metal weight or a packet of lead shot may be placed in each such pocket and thus provide the wearer with an effective weapon to be used in the event of an attack by a dog or another human. Swinging the scarf with the weighted end can provide a substantial blow to any such attacker.

A container for drinking water could obviously be carried in the scarf end pocket, as could a flashlight. The end pocket would make an ideal receptacle for a wallet or a change purse. For people having serious heart problems, a battery powered heart beat/pulse rate monitor could be mounted in the pocket and connected by wire to an appropriate area of the body to monitor the heart beat/pulse rate and sound an alarm if irregularities are detected. Such monitor would, of course, be waterproofed. A two-way radio for maintaining contact with the jogger's or walker's home in case of emergency is also a likely candidate to be carried in the end pocket of the scarf. Other well known accessories, such as a can of mace, a whistle to sound an alarm in the event of trouble, a stop watch, a compass, medical identification, a radio or a cassette tape player could similarly be carried in the end pocket without in any manner interfering with the heat transfer function of the scarf, whether it be heat removal from the neck of the wearer or heat transfer into the neck.

Most of the time the scarf embodying this invention will be worn around the neck of the user, but there is nothing in its construction that would prevent it from being applied to the arm, leg or any other portion of the body where either the application of heat or cold is required. Thus, when a leg muscle strain is encountered during exercise, the scarf can be wrapped around the muscle area to apply a cold pack to the muscle, thus facilitating the relief of the strain. If a particular body area requires heat, then a heat emitting pack can be placed in the pocket of the scarf embodying this invention and the body contacting, heat transmitting wall of the pocket placed against the body area requiring the application of heat.

If it is desired to wear the scarf during rigorous exercise, the scarf may be firmly secured to the body by first wrapping the scarf around the neck and then wrapping the end portions around the chest and securing such ends behind the back by an elastic connector.

Further advantages of the invention will be readily apparent to those skilled in the art from the following detailed description, taken in conjunction with the annexed sheets of drawings, on which are shown several preferred embodiments of the invention.

BRIEF DESCRIPTION OF DRAWINGS

FIG. 10 is a perspective view of another preferred embodiment of the invention utilizing a folded sheet of breathable plastic to form the pocket containing a heat absorbing or emitting mass.

FIG. 11 is a sectional view taken on the plane 11—11 of FIG. 10, with the pocket closing flap in its closed position.

FIG. 12 is an enlarged scale sectional view taken on the plane 12—12 of FIG. 10.

FIG. 13 is an elevational view of a further modification of the scarf shown in FIG. 10, having a skin protective flap overlying the pocket.

FIG. 14 is a view similar to FIG. 13 but with the protective flap being partly folded to its inoperative position.

DESCRIPTION OF PREFERRED EMBODIMENTS

Figure 1:
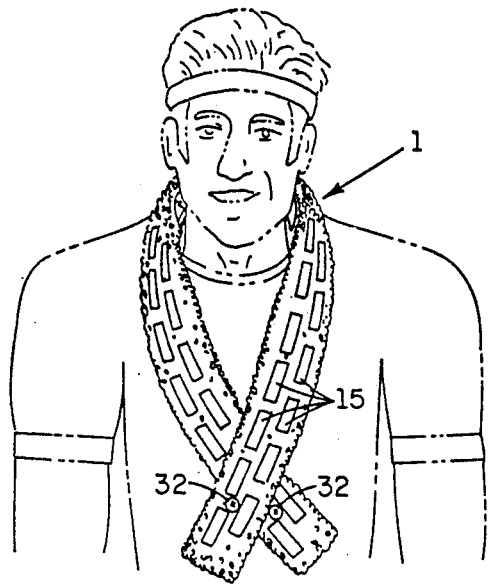
FIG. 1 is a perspective view of a scarf embodying this invention applied to the neck of a wearer.

Referring to FIG. 1, a scarf 1 embodying this invention is usually applied to the neck of the person desiring either cooling after or during exercise, or warming during exposure to cold temperatures. The scarf 1 is preferably formed from cotten toweling material, but can be formed from any fabric material which is capable of being readily sewn and has a significant water absorption capability.

Figure 3:
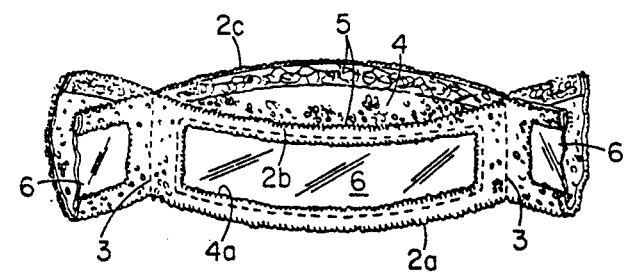
FIG. 3 is a perspective view illustrating the formation of a pocket in the scarf of FIG. 2 for containing a heating or cooling material.
Figure 2:
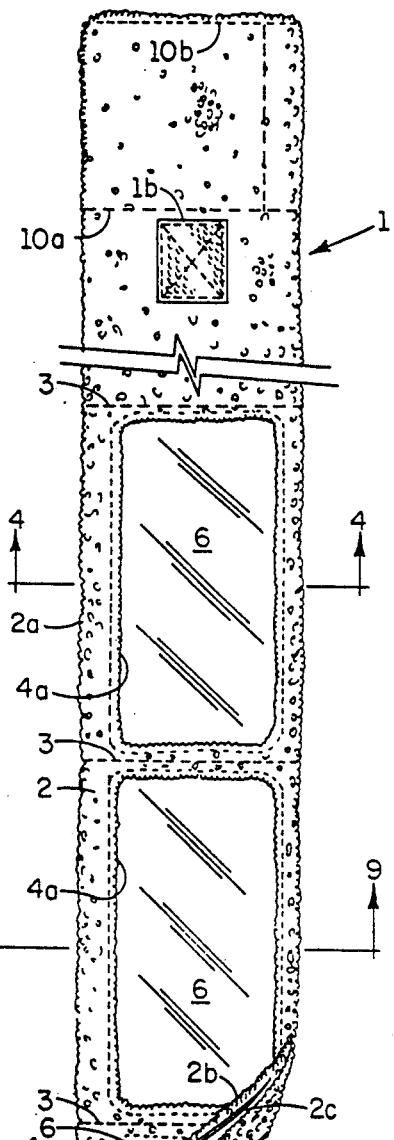
FIG. 2 is an elevational view of the scarf embodying this invention, specifically illustrating the heat transfer windows provided in the scarf.
Figure 2:
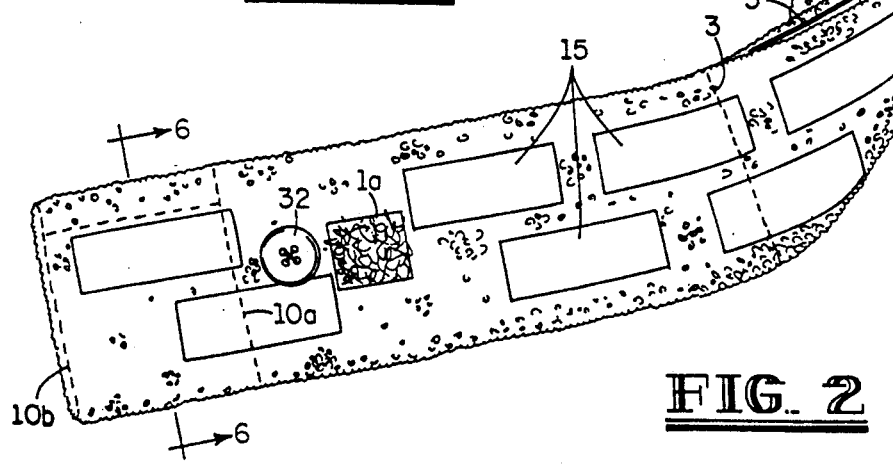

In one preferred form of the invention illustrated in FIG. 2, a length of toweling 2 is folded lengthwise to form a folded edge 2a and overlapping edges 2b and 2c. At longitudinally spaced intervals along the medial portion of the scarf, the overlapped portions of the scarf are transversely secured together in any conventional manner, such as by sewing with threads 3. Discrete pockets 4 are thus formed in the folded toweling material 2 as best illustrated in FIG. 3. The one wall of each pocket 4 is cut away as indicated at 4a to provide an opening of fairly substantial area. A barrier or window 6 of a sheet material having good heat transmitting properties is then sewed or glued across each opening 4a.

A variety of appropriate materials to form the heat transfer window 6 are available in the prior art. Aluminum or tin foil could be employed as could a thin sheet of plastic material. In fact, a thin-walled sheet of fabric could also be employed so long as its heat transmitting properties are substantially better than that of the material of the scarf 1.

Suitable detachable fastening materials 5 are provided along the opposed open edges of each pocket 4. The material sold under the trademark "VELCRO" makes an ideal closure for the pockets 4 but a zipper could obviously be employed.

Figure 4B:
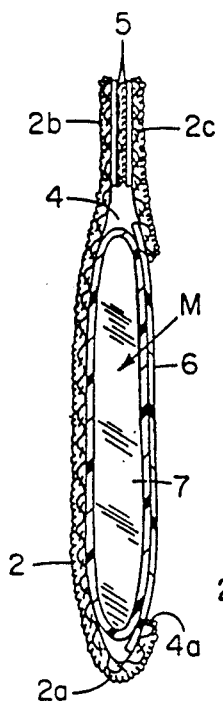
FIG. 4B is a view similar to FIG. 4A but illustrating the use of a gel pack as a heating or cooling material.
Figure 4A:
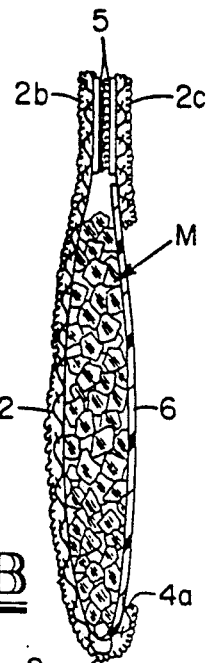
FIG. 4A is an enlarged scale, sectional view taken the plane 4—4 of FIG. 2 illustrating the employment of crushed ice as a cooling material.

A heat emitting or heat absorbing mass M is inserted in each pocket 4 in the manner illustrated in FIGS. 4A and 4B. If the scarf is to be employed for cooling, the heat absorbing mass M may be ice cubes or crushed ice particles as shown in FIG. 4A. If ice particles are not available, a plastic encapsulated gel 7 may be frozen and then inserted in the pocket 4, as shown in FIG. 4B.

Obviously, if the scarf is to be employed for warming purposes, the mass inserted in the pockets 4 would be of the heat emitting type, such as a heated stone, a heated block of light weight metal, or a gel pack which has been heated to an elevated temperature. After insertion of the heat absorbing or heat emitting mass, each pocket 4 is closed by engagement of the reclosable fastening means 5 and the scarf is then wrapped around the neck or any other body part to which it is desired to either remove or apply heat with the window portions 6 of the pocket in contact with such body part. Obviously, the heat transmittal rate through the thin window element 6 is substantially faster than the transmission of heat through the entire thickness of the towelling material 2.

Since one of the principal uses of the scarf embodying this invention is for cooling the neck after exercise, a substantial increase in cooling rate may be achieved by making the window 6 permeable to moisture. This can be done through the incorporation of a plurality of small perforations in the material forming the window 6, or through the utilization of organic sheet material that is specifically designed to be permeable to moisture transmission, such as the plastic sheets employed as innerliners in children's diapers. When this type material is employed for the window 6 and the pocket 4 is filled with ice cubes or crushed ice, it will be apparent that the water melting from the ice will pass through the water permeable material forming the window 6 into direct contact with the neck or other body portion of the user. The cooling effect will therefore be greatly enhanced by virtue of the direct contact of the ice cold water with the skin. The fact that water is applied to the skin is of little consequence to most athletes, since they are generally perspiring heavily and already have a film of moisture on their skin. Furthermore, the water absorbent properties of the towelling 2 from which the scarf is fabricated permits any excess water to be mopped up by the end portions of the scarf.

One heat transmitting material which may be advantageously employed for the heat transmitting window 6 is that previously mentioned organic film sold under the trademark "GORETEX". This film has the advantage of permitting vapors to pass readily through the film into the interior of the pockets 4, thus providing a ready conduit for heat, but at the same time, prevents reverse flow of liquid from the interior of the pocket to the skin, hence the film is called "breathable". Those skilled in the art will recognize that the primary purpose of this invention is to provide a material for window 6 which will produce the ultimate in heat flow from the heat absorbing or heat emitting mass M contained within the pocket 4.

Figure 9:
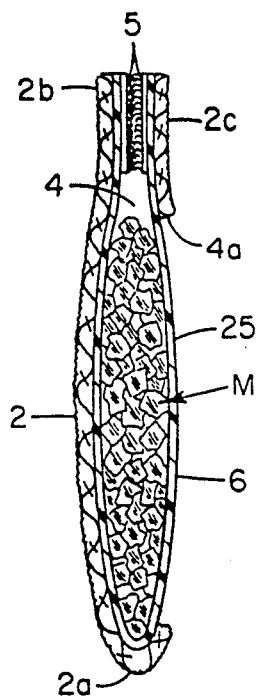
FIG. 9 is a sectional view taken on the plane 9—9 showing a breathable plastic liner for a scarf pocket.

Alternatively, as illustrated in FIG. 9, the entire pocket may be lined with the aforesaid "GORETEX" material 25 to minimize escape of melted ice water. If stitches traverse the GORETEX material, they may be sealed by a suitable coating.

For ordinary cooling or warming purposes, wherein vigorous movement of the body is not involved, the two ends of the scarf 1 may be secured together by patches 1a and 1b of VELCRO secured to the outer end portions of the scarf and brought into securing relationship by the wrapping of the scarf around the neck. For more vigorous activity while wearing the scarf, it may be desirable to employ the modification schematically illustrated in FIG. 7, wherein the ends of the scarf 1 are inserted underneath the armpits to lie adjacent the back of the wearer and the two ends have elastic straps 7a and 7b respectively suitably secured to the scarf ends and detachably secured to each other by any form of conventional fasteners 8. This construction will hold the scarf firmly in position during the vigorous exercise and not interfere with the body or arm movements.

Figure 8:
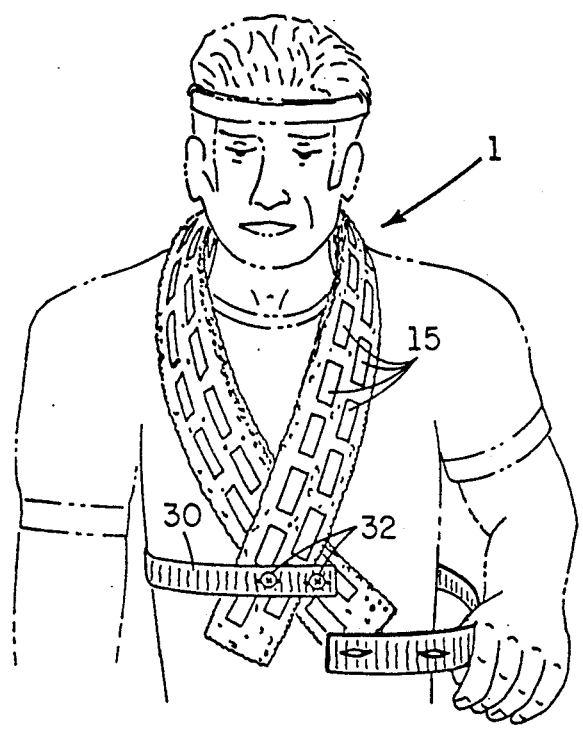
FIG. 8 is a perspective view of a front fastened elastic strap for securing a scarf.

Alternatively, as shown in FIG. 8, the ends of the band may be secured by buttons 32 to an elastic band 30 which snugly engages the waist of the user.

Figure 5:
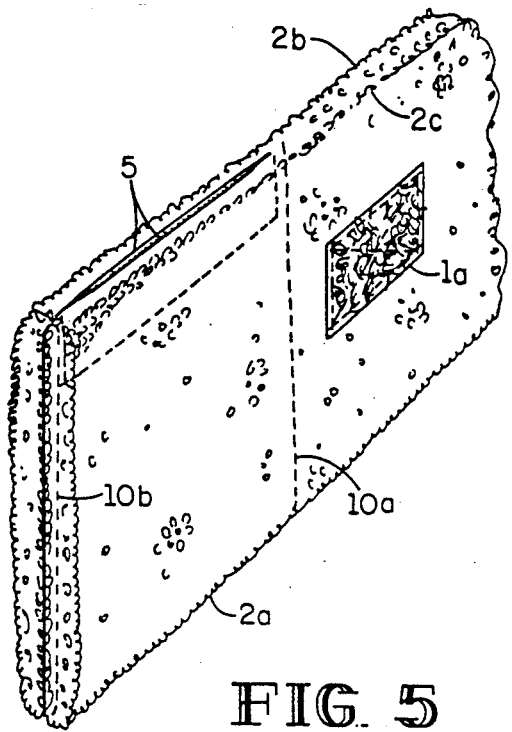
FIG. 5 is an enlarged scale view of the end portion of the scarf showing the formation of an end pocket.
Figure 6:
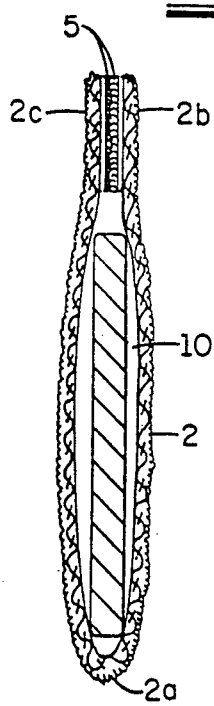
FIG. 6 is a sectional view taken on the plane 6—6 of FIG. 5 illustrating the mounting of an exercise accessory in the end pocket.

A further modification of this invention involves the provision in each end of the scarf of an accessory pocket 10 (FIGS. 5 and 6). The accessory pocket may be produced by transverse sewing 10a accompanied by the application of VELCRO strips 5, or a zipper, to the overlapped end portions 2b and 2c of the toweling material 2. A reclosable end pocket 10 is preferably formed in both ends of the scarf 1. The end pocket 10 may be employed to house any exercise accessories, particularly accessories useful for joggers and walkers. Thus, as shown in FIG. 6, the end pocket 10 may house a relatively heavy stone or piece of metal 12 which will effectively convert the scarf 1 into a defensive weapon to ward off attacks by dogs or humans. Holding onto one end of the towel while swinging the weighted other end of the towel creates a good defensive barrier as well as an offensive weapon.

Figure 7:
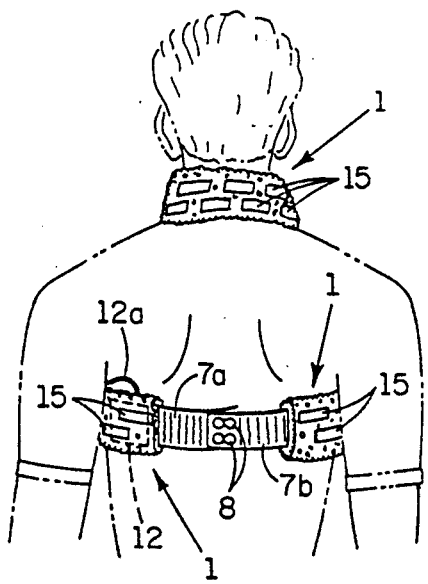
FIG. 7 is a perspective view illustrating a more secure attachment of the scarf to the body of the wearer by the use of a back fastened elastic strap.

As illustrated in FIG. 7, pocket 10 may incorporate a heart beat/pulse rate monitor 12 which would be connected by a lead 12a to an ear or finger clip (not shown) or to one or more suction cups (not shown) applied to an appropriate portion of the wearer's chest. The heart beat/pulse rate monitor 12 would preferably be of the type that would sound an alarm if a predetermined pulse rate is exceeded, or an irregular heart beat is detected during the walking or jogging.

As previously stated, other well known accessories, such as a drinking water container, a flashlight, a wallet or change purse, a can of Mace, an alarm whistle, a stop watch, a compass, medical identification, a radio or a cassette tape player could similarly be carried in the end pockets 10 without in any manner interfering with the heat transfer function of the scarf, whether it be heat removal from the neck of the wearer, or heat transfer into the neck.

To enhance visibility of the wearer at night, bright colored strips or patches 15 of reflecting material may be applied to the outer surface of the scarf 1 as shown in FIGS. 1 and 7.

Another preferred modification of this invention is illustrated in FIGS. 10-14. An elongated strip of flexible, water absorbent material, such as a single or a folded length 50 of towelling forms the scarf. An elongated pocket 52 of breathable plastic, such as the aforementioned plastic material sold under the trademark "GORETEX" is formed by folding a sheet of such material into a pocket or envelope configuration. Thus, as shown in FIGS. 10, 11 and 12, each pocket 52 is folded to form a longitudinal edge 52a and has its transverse edges 52b folded as indicated at 55 and sewn to the scarf 50 by threads 55a.

A sealable thread 60 is sewed transversely across each transverse edge 52b of pocket 52 interiorly of threads 55a, and extends longitudinally along the abutting longitudinal pocket edges 52c to the respective end of an opening 56.

The longitudinal opening 56 is closed by folding an integral flap 57 over opening 56 and removably sealing flap 57 to the innerface 52e of the pocket 52. A water proof version of "VELCRO" (TM) fastener strips 58 can be employed for the removable seal. The transverse stitching 55a by which pocket envelope 52 is secured to the medial portions of the towelling 50 passes through the "GORETEX" material outside of the sealable stitching 60. Additional securement can be provided by stitching (not shown) outside of the longitudinal portions of sealable stitching 60. All sealable stitches are waterproofed by a suitable liquid plastic (not shown) which solidifies after application, or by utilization of a sealable tape sold under the trademark GoreSeam by the aforementioned W. L. Gore and Associates and applied by a GoreSeam Sealing Machine.

Ice cubes, ice particles, or a frozen gellpack is inserted in the pocket 52 and the scarf is applied to the neck or other body part where cooling is desired. Due to the unique properties of "GORETEX" material, a rapid flow of heat from the adjacent body part, and heated vapor passes through the "GORETEX" material to the coolant contents of pocket 52. Alternatively a heated mass may be inserted in pocket 52.

The cooling may be so rapid as to produce an irritation for persons having sensitive skin. The modification of FIGS. 13 and 14 shows a scarf 50 and a "GORE-TEX" pocket 52 with an extra length of towelling 66 transversely sewn at one end 66a to the scarf 50 so that it may be selectively positioned to overlie the pocket 52, as shown in FIG. 13, and thus protect the body part from excessive cooling. If such protection is not desired, the extra towelling length 66 is folded in the reverse direction (FIG. 14) to expose the side wall 52e of the "GORETEX" pocket 52 for direct contact with the body part around which the scarf 50 is wrapped. It is readily apparent that the heat transfer function performed by the scarf could be readily applied to other portions of the body, such as an arm or leg, in order to relieve muscle strain or reduce a fever by the application of the cooling action of the scarf, or to apply heat if a particular body area requires such application.

Figure 15:
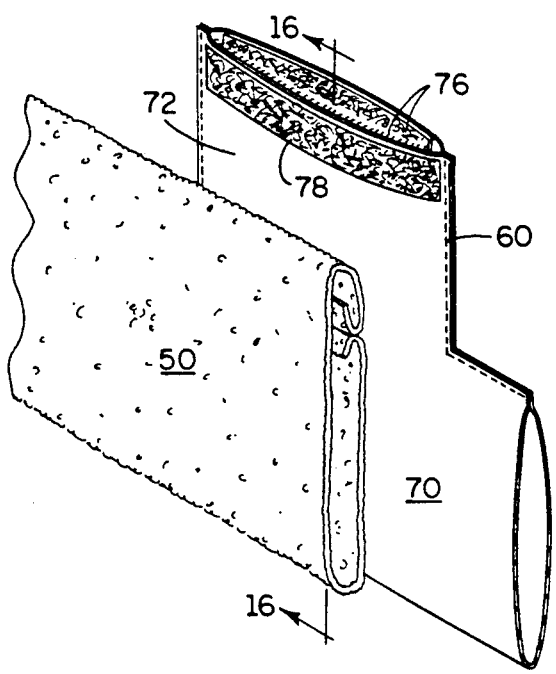
FIG. 15 is a perspective view of a GORETEX envelope formed with modified closing flaps for sealing the opening.
Figure 16:
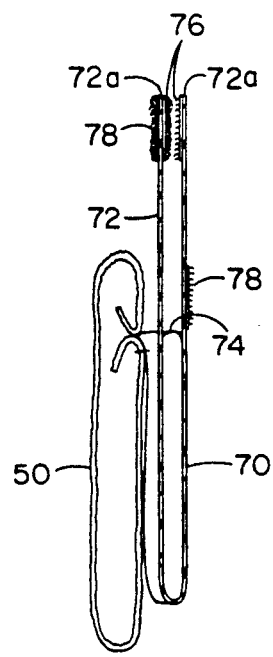
FIG. 16 is a sectional view of FIG. 15 taken on the plane 16—16.
Figure 17:
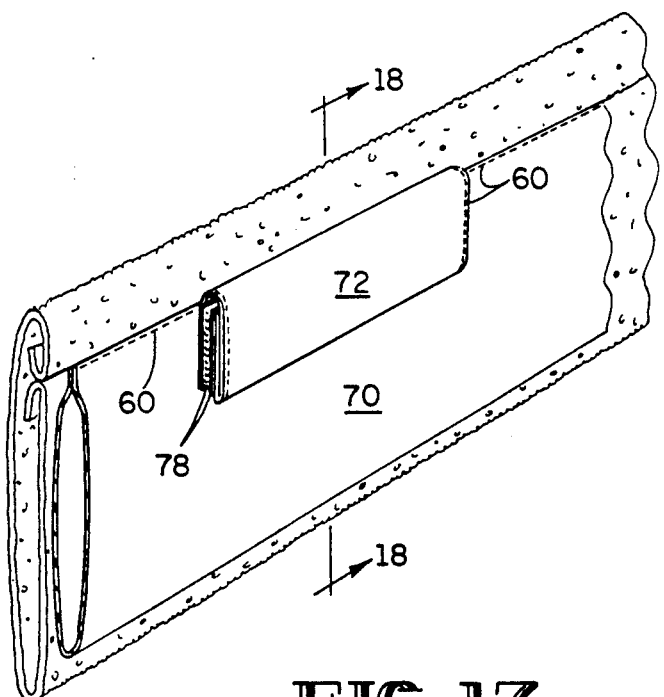
FIG. 17 is a view similar to FIG. 15 but showing the final securement of the roll-folded closing flaps.
Figure 18:
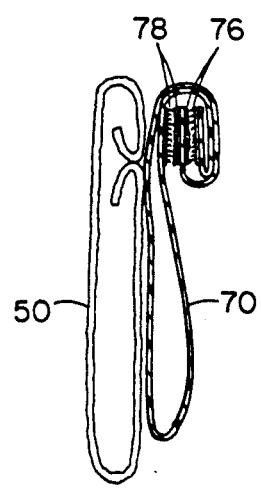
FIG. 18 is a sectional view of FIG. 17 taken on the plane 18—18.

Referring now to FIGS. 15-17, there is shown another embodiment of this invention which improves the sealing of the interior of the pocket or envelope which contains ice particles or frozen gell pack. In this modification, the envelope or pocket 70 is provided on both its front and rear faces with similar flaps 72 adjacent the pocket opening but project substantially beyond the pocket opening 74. The previously mentioned sealable thread stitches 60 are extended along both lateral edges of flaps 72 and are sealed by internally applied "Gore Seam" (#) tape. The flap ends 72a are secured together by VELCRO strips 76, preferably of the waterproof variety. The secured flaps 72 are then folded or rolled several times as shown in FIG. 17 to bring the outer ends 72a of the folded flaps 72 into general alignment with the top of the pocket 70. The roll-folded flaps 72 are secured to the inner face of envelope 70 by a second set of VELCRO strips 78. This construction greatly improves the leakage resistance over that provided by the single closing flap previously described.

Although the invention has been described in terms of specific embodiments, it should be understood that this is by way of illustration only and that the invention is not necessarily limited thereto, since alternative embodiments will become apparent to those skilled in the art as a result of this disclosure.

What is claimed and desired to be secured by Letters Patent is:

1. A scarf for transferring heat from a body part encircled by the medial portions of the scarf comprising:

an elongated band of flexible fabric material;

a pocket secured to the medial portions of said band on the side thereof adjacent the body part, whereby one external surface of said pocket is adjacent said body part;

said pocket having an opening, thereby permitting the insertion of a mass of coolant material in said pocket; and means for repeatably closing said opening;

said pocket being formed by a sheet of a moisture impervious, breathable, flexible plastic material, thereby producing substantial heat and vapor flow from said body part to said coolant mass while trapping water within said pocket. pocket.

2. The apparatus of claim 1 wherein said means for closing said pocket comprises:

an integral flap of said moisture impervious, breathable, flexible plastic material formed on said pocket and foldable over said pocket opening; and means for sealingly securing said flap across said pocket opening.

3. The scarf of claim 1 wherein said pocket comprises:
a rectangular envelope having a back side secured to said medial portions of said band and a front side adapted to contact a body part;
said opening being located along the longitudinal juncture of said front and back sides.

4. The scarf of claim 3 wherein said means for closing said opening comprises a pair of integral flaps of said moisture impervious, breathable, flexible plastic material formed on said front and back sides of said pocket adjacent to and with the same width as said opening and extending substantially beyond said opening;
means for releasably securing the outer edges of said flaps together;
said flaps being rolled toward the envelope to bring the rolled flaps adjacent the front face of said envelope; and
means for detachably securing said rolled flaps to the front face of said envelope.

5. The scarf of claim 1 further comprising:
a second elongated band of flexible fabric material having a peripheral configuration conforming to but exceeding all similar dimensions of said pocket; and
means for transversely securing said second band to said first mentioned band at a location adjacent one edge of said pocket, whereby said second band may overly the body adjacent wall of said pocket to provide a heat insulating barrier between said body part and said mass of ice particles.

6. The scarf of claim 1, 2, 3, 4, or 5 wherein said flexible fabric material comprises towelling.

7. The scarf of claim 1 wherein said pocket is formed from a generally rectangular sheet of said moisture impervious, breathable, flexible plastic material folded into the configuration of a rectangular envelope having a folded longitudinal edge, an opening along the opposed longitudinal edge, and at least one integral longitudinal flap foldable into closing relation to said opening;
the transverse end portions of said envelope being sealably secured together adjacent the transverse edges of said envelope, thereby defining sewing flaps for securing said envelope to said band.

8. The scarf of claim 7 further comprising means for releasably securing said flap across said opening.

9. The scarf of claim 8 wherein said means for releasably securing said flap across said opening comprises a second integral flap secured to a side of said envelope opposite to said first mentioned flap and disposed in overlying relation to said first mentioned flap;
means for releasably securing the outer edges of said flaps together to permit said flaps to be roll folded into adjacent relationship to the side of said envelope adjacent the body part.

10. A scarf for absorbing heat from or transmitting heat to a body area of the wearer comprising:
an elongated band of flexible fabric material wrappable around the body area of a wearer;
a pocket secured to a medial portion of said fabric band;
said pocket being formed by folding a sheet of moisture impervious, breathable plastic material to provide an outer flat face abuttable with said fabric band and an inner face abuttable with said body area of the wearer;
said pocket having an opening permitting the insertion of a mass of heat absorbing or heat transmitting material to selectively cool or heat said body area.

11. The scarf of claim 10 further comprising at least one integral flap on said pocket foldable into closing relation with said pocket opening; and
means for releasably securing said flap in said closing relation with said pocket opening.

* * * * *